United States Patent [19]

Mason et al.

[11] Patent Number: 5,612,040
[45] Date of Patent: Mar. 18, 1997

[54] NON-INFECTIOUS FOOT-AND-MOUTH DISEASE VIRUSES

[75] Inventors: Peter W. Mason, Killingworth, Conn.; Barry Baxt, Port Jefferson Station, N.Y.; Elizabeth Reider, Westbrook, Conn.; Analia Berinstein, Capital Federal, Argentina; Angray S. Kang, Carlsbad, Calif.

[73] Assignee: The United States of America as represented by the Secretary of Agriculture, Washington, D.C.

[21] Appl. No.: 418,716

[22] Filed: Apr. 7, 1995

[51] Int. Cl.$^6$ .......................... A61K 39/135; C12N 7/04; C12N 7/06; C07H 21/02
[52] U.S. Cl. .................... 424/205.1; 424/216.1; 435/238; 435/236; 536/23.72
[58] Field of Search ........................ 424/216.1, 205.1; 435/236, 238; 514/44; 536/23.72

[56] References Cited

PUBLICATIONS

Carreño et al. "Studies on antigenic variability of C Strains of foot–and–mouth disease virus by means of synthetic peptides and monoclonal antibodies" *Int. J. Peptide Protein Res.* 39, 1992, pp. 41–47.

Mason et al., *Proc. Natl. Acad. Sci.*, vol. 91, pp. 1932–1936 (1994).

Novella et al., *FEBS Letters*, vol. 330(3), pp. 253–259 (1993).

Rieder et al., *Journal of Virology*, vol. 67(9), pp. 5139–5145 (1993).

*Primary Examiner*—Robert D. Budens
*Assistant Examiner*—Phuong T. Bui
*Attorney, Agent, or Firm*—M. Howard Silverstein; John Fado; Janelle S. Graeter

[57] ABSTRACT

A safe, effective vaccine for the protection of susceptible animals against foot-and-mouth disease has been produced. The vaccine comprises a mutant virus from which the amino acid sequence Gly-Val-Arg-Gly-Asp-Phe (SEQ ID NO: 8) from the G-H loop of VP1 has been deleted and replaced with the amino acid sequence Asn-Pro. The mutant virus retains its antigenicity but is not infectious.

5 Claims, 2 Drawing Sheets

Amino Acid Residue in VP1

```
           130        140        150        160
           *          *          *          *
pRMC35     Y NGTNKYSASG SGVRGDFGSL APRVARQLPA    SEQ ID NO: 1 pRM-DRGD   - ---------- --D------- ----------   SEQ ID NO: 2
pRM-PRGD   - ---------- --P------- ----------   SEQ ID NO: 3
pRM-RGDK   - ---------- ------K--- -L--------   SEQ ID NO: 4 pRM-KGD    - ---------- ---K------ ----------   SEQ ID NO: 5
pRM-RGE    - ---------- -----E---- ----------   SEQ ID NO: 6
pRM-KGE    - ---------- ---K-E---- ----------   SEQ ID NO: 7
```

Fig. 1

NON-INFECTIOUS FOOT-AND-MOUTH DISEASE VIRUSES

BACKGROUND OF THE INVENTION

1. Field of the Invention

Foot-and-mouth disease virus (FMDV) is responsible for one of the most devastating and contagious diseases in cattle and other cloven-hooved animals, affecting over 100,000 animals a year and resulting in significant economic loss. The disease occurs in many areas of the world outside the United States where vaccination programs have been largely effective. There are risks associated with the vaccines currently in use, however, and at present FMDV vaccines cannot be produced in the United States despite the continued threat of the introduction of this agent into the country. It is feared that the virus used to make vaccines could escape from containment and cause disease. Moreover, the failure to completely inactivate the virus during vaccine preparation has led to accidental outbreaks of infection. In addition, there is considerable antigenic variability among the various serotypes, thus some viruses may not be recognized by the vaccinated animals. Furthermore, frequent revaccination has been required in order to maintain protective immunity utilizing conventional vaccines containing virus attenuated by chemical inactivation (Bachrach, H. L. 1968. *Annu. Rev. Microbiol.* vol. 22, pp. 201–244). There is thus a strong incentive to develop an effective vaccine which eliminates the threat of infection due to the accidental outbreaks associated with vaccine production and administration. This invention relates to a new and safer vaccine against FMDV which provides effective protection but is not infectious, and thus does not present the risk of causing accidental infections.

2. Description of the Prior Art

In an effort to overcome the deficiencies of conventional virus vaccines, synthetic vaccines have been investigated. Identification of a flexible loop exposed on the virus surface as the main antigenic site of FMDV (site A) prompted the investigation of the use of various peptide fragments within site A to stimulate immunological responses. For example, the conserved tripeptide Arg-Gly-Asp (RGD) was evaluated for its ability to stimulate the production of neutralizing antibodies in rabbits or guinea pigs (Novella et al. 1993. *FEBS Letters.* vol. 330, no. 3, pp. 253–259).

Attempts to produce attenuated virus vaccines by genetic engineering were also carried out. Rieder et al. (1993. *J. Virol.* vol. 67, no. 9, pp. 5139–5145, herein incorporated by reference), for example, evaluated the role of the poly(C) tract found at the 5' end of the FMDV genome. Cardioviruses having shorter-than-natural poly(C) tracts had been shown to be dramatically attenuated; however, the poly(C) tract length of FMDV showed no effect on virulence when tested in mice.

Thus, the search for an improved vaccine has continued.

SUMMARY OF THE INVENTION

We have discovered that a novel foot-and-mouth disease virus can be prepared by deletion of the nucleic acid sequence encoding the cell binding site from an infectious cDNA copy of the genome, resulting in a virus which retains its immunogenicity but is not infectious. In accordance with this discovery, it is an object of the invention to provide a novel genetically-engineered virus vaccine which provides protective immunity against foot-and-mouth disease but is not infectious.

It is another object of the invention to provide a method of conferring immunological protection against foot-and-mouth disease by administering the novel vaccine.

Other objects and advantages of the invention will become readily apparent from the following description.

BRIEF DESCRIPTION OF THE DRAWINGS

FIG. 1 shows the amino acid sequences of the G-H loop of the wild-type and mutant genomes. Dashes designate identity with wild-type.

DETAILED DESCRIPTION OF THE INVENTION

Figure 2:
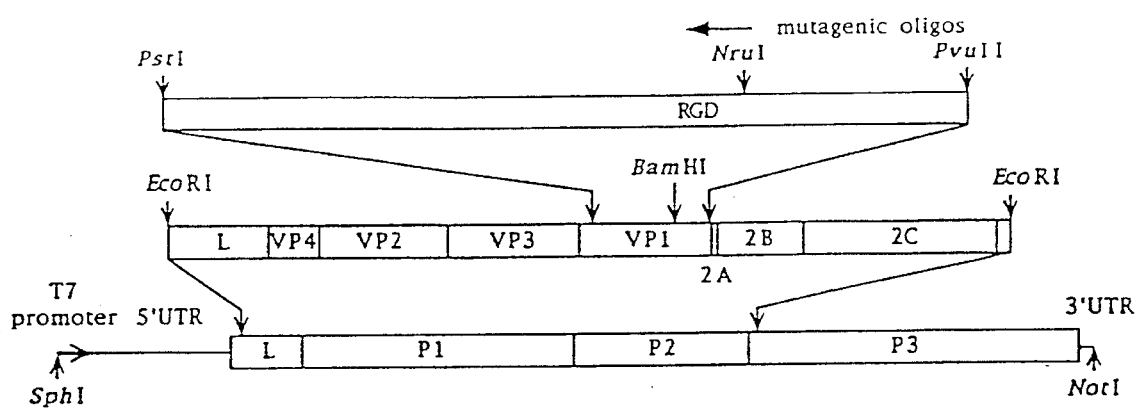
FIG. 2 shows the position of mutated sequences on the FMDV genome. cDNA fragments used to engineer mutant viruses are shown above the FMDV portion of the plasmid pRMC$_{35}$. UTR, untranslated region; oligos, oligonucleotides.

A vaccine is defined herein as a biological agent which is capable of stimulating a protective immune response in an animal to which the vaccine is administered.

Foot-and-mouth disease virus is an RNA virus of the Aphthovirus genus of the family Picornaviridae. There are several known serotypes occurring in Europe (A, O and C serotypes), southern Africa (SAT 1, SAT 2 and SAT 3) and the Asia 1 serotype, having distinct variations both immunologically and genetically. The virion consists of a single-strand, positive-sense RNA genome packaged in an icosahedrally symmetric shell composed of 60 copies each of four structural proteins, VP1-4. Analysis of the three-dimensional structure of FMDV revealed a prominent surface feature formed by a flexible loop between the G and H β strands of VP1 (G-H loop)(Acharya et al. 1989. *Nature.* volo. 337. p. 709; Parry et al. 1990. *Nature.* vol. 347, p. 569; Logan et al. 1993. *Nature.* vol 362, p. 566). Contained within this loop is the highly conserved RGD tripeptide sequence which has been identified as the main antigenic site. In addition, synthetic peptide inhibition studies have suggested that the site is also involved in receptor binding activity (Fox et al. 1989. *J. Gen. Virol.* vol. 70, p. 625; Baxt and Becker. 1990. *Virus Genes.* vol. 4, p. 73).

Studies were carried out in order to further elucidate requirements for cell binding, immunogenicity and the infectious ability of the virus. For this purpose, mutant viruses were prepared from a full-length infectious cDNA clone of FMDV type A$_{12}$ (Rieder et al., supra), where amino acid substitutions were made either within or bordering the conserved RGD sequence (as described in Mason et al. 1994. *PNAS.* vol. 91, pp. 1932–1936, herein incorporated by reference).

Full-length mutant cDNA molecules having sequence changes as shown in FIG. 1 in codons 143–147 of VP1 were produced. Antigenic properties of mutant viruses produced from the cDNAs were evaluated by reacting the viruses with a panel of monoclonal antibodies which recognized epitopes either within or outside the G-H loop. Results, shown in Table 1, indicated that conservative changes within the G-H loop did not induce major changes in the antigenic structure of the virion.

TABLE I

| Sequence* | Antibody Reactivity** | Cell Binding, %+ |
| --- | --- | --- |
| VRGDF (Wild-type) | + | 65 |
| DRGDF | + | 28 |
| PRGDF | + | 61 |
| VRGDK‡ | ± | 63 |
| VKGDF | + | 2 |
| VRGEF | + | 2 |
| VKGEF | + | 2 |

*Amino acids 143–147 of VP1 (underline denotes mutations)
**Determined by radioimmunoprecipitation: +, strong reaction, ±, weak reaction
+Determined at a constant virus/cell ratio (1000:1)
‡Also contains a leucine substitution for a proline at position 152 (see FIG. 1)

Cell binding studies utilizing the mutant viruses were also carried out. Binding of the viruses having mutations bordering the RGD sequence to baby hamster kidney (BHK) cells were retained; however, cell binding was somewhat reduced in two of the three mutants and reduced by about 50% in the third. Those mutants having mutations within the RGD sequence did not bind to BHK cells, however, indicating that they were defective with respect to binding and adsorption into the cell (Table 1).

Transcripts of the various mutant sequences were evaluated for their ability to cause cytopathic effects (CPE) and produce plaques following transfection into BHK cells. Those transcripts having mutations bordering the RGD sequence caused CPE, plaques and specific infectivities similar to transcripts from the parental infectious clone (Table 2), indicating that mutations encoded by these RNAs had no effect on viability.

The mutant viruses were found to be antigenic but not infectious, however single base mutations have been known to revert to wild-type. Tests were thus carried out to determine if reversions occurred as expected for the mutant viruses. Cells transfected with mutant RNA containing KGD and RGE mutations were found to produce 10,000-fold less infectious virus than cells transfected with RNA produced from the wild-type virus. Sequence analysis of selected plaques harvested from transfected cells confirmed that those viruses found to be infectious had regained the RGD coding sequence. As also expected, the double mutation KGE did not appear to revert to wild-type since no plaque-forming units were recovered from cells transfected with the double-mutant RNA. In addition, all of the KGD and RGE revertants produced wild-type plaques, and a detailed examination of cell binding by one of these revertants revealed that it bound to cells as well as the wild-type virus, conclusively showing that the RGD sequence is required for adsorption to and infection of BHK cells.

TABLE II

| Sequence* | Specific Infectivity** |
| --- | --- |
| VRGDF (Wild-type) | $4.2 \times 10^3$ |
| DRGDF | $6.6 \times 10^3$ |
| PRGDF | $2.0 \times 10^3$ |
| VRGDK | $1.4 \times 10^3$ |
| VKGDF | <1 |
| VRGEK | <1 |
| VKGEF | <1 |

*Amino acids 143–147 of VP1 (underline denotes mutation)
**Specific Infectivity of transcripts (plaque-forming units/µg) determined using Lipofectin Since the threat of reversion to wild-type is clearly not a desirable property for a virus contemplated for use as a vaccine, especially one having virulence such as that exhibited by FMDV, efforts to create a stable non-infectious FMDV were begun. A virus was constructed in which the entire RGD sequence was deleted, and tests were carried out to determine the effect of the deletion on the conformation of the capsid structure, and thus the antigenicity of the virus. A genome-length cDNA (Rieder et al., supra) was prepared from the wild-type RNA, and the codons encoding the wild-type amino acid sequence GVRGDF were replaced with codons for AsnPro (NP). Synthetic RNA transcripts were constructed from this cDNA and introduced into BHK cells (Mason et al., supra). Cells transfected with the synthetic RNA produced levels of virus particles similar to those produced by cells transfected with wild-type RNA, and preliminary experiments showed that these particles did not bind to cells, were noninfectious, and were recognized by monoclonal antibodies specific for four different epitopes on FMDV type $A_{12}$ (Baxt et al. 1984. *J. Virol.* vol. 51, p. 298; Baxt et al. 1989. *J. Virol.* vol. 63, p. 2143). One of these epitopes included portions of the G-H loop, indicating that the deletion had little, if any, effect on the antigenic structure of the RGD-deleted virus.

Tests were also carried out to demonstrate that the RGD-deleted mutant viruses would not revert to wild-type with respect to infectivity or virulence (see Example 2). RGD-deleted mutant virus preparations were used to inoculate BHK cells and baby mice. No CPE were observed in BHK cell cultures which had been incubated for 72 h, and a plaque assay carried out on passaged cells did not reveal any infectious agent. In addition, 20 7- to 10-day-old mice were inoculated, and none of the mice died or showed any signs of infection.

Virulence of the mutant virus was tested by inoculating swine with either mutant or wild-type virus (see Example 3). Virus was inoculated into the coronary band and the dermis of the snout of two adult Yorkshire swine, and the animals were observed for signs of FMD for 2 weeks. Symptoms of classical FMD were observed in the animal having received the wild-type inoculation, whereas the animal receiving mutant virus inoculations showed no signs of disease.

Tests were also carried out to demonstrate the efficacy of the vaccine (see Example 4). A vaccination/challenge study with nine 18- to 20-month-old steers was conducted. Three steers were mock vaccinated, three animals were vaccinated with a conventional inactivated wild-type virus and the remaining three animals were vaccinated with the mutant RGD-deleted virus. The animals were observed for signs of disease for 4 weeks, and none showed any development of disease.

To further test the effectiveness of the mutant virus, the nine animals were subsequently combined in a single room and exposed to a pig which had developed severe clinical manifestations of FMD. The cattle were examined daily for signs of the disease. All six vaccinated animals were protected whereas all three mock-vaccinated animals demonstrated clinical FMD within 7 days of exposure to the infected pig.

Preparation of the mutant virus is carried out by conventional genetic engineering techniques which are well-established in the art (as described, for example, in *Current Protocols in Molecular Biology.* 1994. Ausubel et al., eds. J. Wiley & Sons, N.Y.). The preparation steps include 1) synthesizing cDNA from infectious RNA, 2) replacing the sequences coding for GVRGDF with NP, 3) transcribing RNA containing the deleted sequences from the mutant cDNA, 4) cloning the mutant synthetic RNA into an effective vector, 5) transfecting cells capable of allowing assembly of the mutant virus from the vector containing the mutant RNA, 6) allowing the RNA to replicate in the transfected cells in order to produce mutant virus particles and 7) harvesting the mutant virus particles from the cell cultures.

Infectious RNA is obtained by purification from FMDV preparations (as described by Baxt et al., 1984, supra) and used as a template for reverse transcription to produce cDNA. The second DNA strand is then generated by a DNA-dependent DNA polymerase using standard techniques (Ausubel et al., supra). Effective polymerases include Klenow, DNA polI or Taq polymerase (NEB, Beverly, Mass.; Boehringer Mannheim, Indianapolis, Ind.; GIBCO/BRL, Gaithersburg, Md.). The DNA products are either directly molecularly cloned into an effective plasmid or amplified by the polymerase chain reaction prior to molecular cloning (Ausubel et al., supra). Effective plasmids include but are not limited to those derived from *Escherichia coli* (*E. coli*) such as the pGEM plasmids (Promega, Madison, Wis.). Plasmids containing virus cDNAs are assembled into genome-length cDNA molecules (Ausubel et al., supra). Some regions of the genome, specifically the extreme 5' end, the extreme 3' end and the poly C tract found near the 5' end of the genome may be produced from synthetic DNA molecules, based on known or predicted sequence data (Rieder et al., supra). cDNA molecules corresponding to the full-length FMDV genome are then placed under the control of an effective promoter (for example positioned behind the DNA sequence of the T7 bacteriophage polymerase promoter) in a bacterial plasmid vector (such as one derived from pGEM3). Plasmid DNA molecules containing the full-length cDNA are purified from cultures of the *E. coli* harboring the plasmids (Ausubel et al., supra), and the purified DNA is used as a template for RNA polymerase to produce synthetic genome-length RNAs containing insertions deletions or mutations in the viral genome (Rieder et al., supra). An effective RNA polymerase has been found to be T7 RNA polymerase (GIBCO/BRL, Promega or Ambion, Austin, Tex.).

The synthetic RNA is effectively constructed from the cDNA sequences in which GVRGDF codons have been replaced with those encoding NP. This change occurs in codons 142–147 of VP1 as shown in FIG. 2. The mutation may be introduced into a PstI-PvuII fragment comprising most of VP1, by use of an existing NruI site. Alternatively, mutations are introduced into a plasmid containing a 4.26-kb EcoRI fragment by using a BamHI site added by the addition of silent mutations at codon 148 of VP1 (FIG. 2).

cDNA molecules containing the specific change in codons 142–147 are then prepared using standard polymerase chain reaction procedures (Rieder et al., supra; Higuchi et al. 1988. *Nucleic Acids Res.* vol. 16, pp. 7351–7367), and the entire amplified region sequenced, for example with Sequenase (United States Biochemicals).

Mutated fragments are then introduced into a full-length infectious clone by any standard technique which is effective (for example as described by Ausubel et al., supra). The mutations are then resequenced in order to ensure that the required mutation is maintained.

RNAs are transcribed, for example from a NotI-linearized plasmid such as that shown in FIG. 2. A Megaprep T7 kit (Ambion, Austin, Tex.) or the method described by van der Werf et al.(1986. *PNAS.* vol. 83, pp. 2330–2334, herein incorporated by reference) have been found to be effective for this purpose. The synthetic RNAs are then introduced into cells capable of allowing replication the mutant viruses.

BHK cells have been found effective for this purpose; however, other cell lines such as Chinese hamster ovary (CHO) are also useful. The cells may be effectively transfected using Lipofectin (GIBCO/BRL) or electroporation as described in Mason et al., supra.

Using the electroporation method described in Example 1, large numbers of cells transfected with the RGD-deleted RNA are produced, cultured and mutant virus particles are found in the culture medium. Any effective culture medium may be used, for example Eagle's minimum essential medium with 10% calf serum and 10% tryptose phosphate broth, supplemented with antibiotics. The mutant virus may then be harvested from the cultures and purified for use as a vaccine.

Vaccines are prepared for inoculation by mixing an effective immunization dosage of the mutant virus in a pharmaceutically acceptable carrier or diluent, such as physiological saline or tissue culture medium. An effective immunization dosage is defined as that amount which will induce immunity in an animal against challenge by a virulent strain of FMDV, and immunity has been considered having been achieved when the level of protection for the immunized population is significantly higher than that of an unvaccinated control group. An effective dosage is easily determined by one of skill in the art for the paricular animal of interest by administering varying amounts of the vaccine preparation to test animals and observing the dosage at which protection has been achieved.

In addition, appropriate adjuvants as known in the art may also be included in the vaccine formulation.

The following examples are intended only to further illustrate the invention and are not intended to limit the scope of the invention as defined by the claims.

EXAMPLES

Example 1

Preparation of Synthetic Mutant FMDV.

FMDV RNA is isolated and purified from FMDV and used to produce cDNA by reverse transcription using AMV reverse transcriptase (Boehringer Mannheim) or Moloney murine leukemia virus (MMLV) reverse transcriptase (GIBCO/BRL). Mutations in the cDNA molecule are carried out according to the method presented in FIG. 2. Double-stranded DNA is then produced by filling in with DNA-dependent DNA polymerase and is cloned into the pGEM plasmid. Plasmids containing virus cDNAs are identified and assembled into genome-length cDNA molecules and placed under the control of the T7 bacteriophage polymerase promoter. Plasmid DNA molecules containing the full-length cDNA are purified from cultures of *E. coli* which harbor the plasmids, then used as a template for T7 RNA polymerase to produce synthetic genome-length RNAs containing the RGD deletion in the viral genome.

Electroporation is carried out by mixing 0.8 ml BHK cells at $3 \times 10^7$ cells per ml of $Ca^{2+}$- and $Mg^{2+}$-free phosphate buffered saline with 10 to 20 µg of RNA in a 0.4-cm cuvette, pulsed twice at 1500 V and 14 µF in an IBI Gene Zapper (IBI, New Haven, Conn.), diluted with growth medium (Eagle's MEM, 10% calf serum) and incubated in culture plates for 2–4 hours prior to removal of unattached cells and incubation overnight at 37° C.

The virus particles present in the culture fluid are harvested from the BHK cell cultures, concentrated by polyethylene glycol precipitation and further purified by sucrose density gradient centrifugation (Baxt et al., 1984 and 1989, supra).

The amount of virus present in these partially purified preparations was estimated by comparison of the radioactive signals obtained on Western blots (Towbin et al. 1979. *PNAS.* vol. 76, p. 4350) with two-fold dilutions of a known concentration of wild-type virus, detected using polyclonal guinea pig serum specific for FMDV and $^{125}$I-labeled protein A (NEN, Boston, Mass.). Approximately 1 µg of partially purified RGD-deleted virions could be obtained from $6\times10^6$ transfected cells.

Example 2

Inoculation into BHK Cells and Mice.

BHK cells and baby mice were inoculated with the RGD-deleted virus preparations in order to demonstrate that the RGD-deleted virus would not regain its infectivity or virulence. Five hundred ng of RGD-deleted virus were diluted in culture media, inoculated into cultures of BHK cells, and incubated for 72 h at 37° C. Although no cytopathic effect (CPE) was visible at this time, the sample was lysed by freeze-thaw, and passaged onto fresh cells. A plaque assay of this second passage material on BHK cells did not reveal any infectious agent. One hundred ng of RGD-deleted virus were inoculated intraperitoneally (IP) into 20 seven- to ten-day-old mice. None of these mice died or showed any signs of infection. One hundred ng of a wild-type virus prepared from cells transfected with RNA derived from the wild-type genome-length cDNA, pRMC$_{35}$ (Rieder et al., supra), is equivalent to $1.2\times10^6$ mouse LD$_{50}$. These results demonstrate that the RGD-deleted virus is attenuated greater than $1\times10^6$ fold relative to wild type.

Example 3

Inoculation of Swine.

Two µg of either wild-type or RGD-deleted virus were inoculated into the coronary band and the dermis of the snout of two adult Yorkshire swine. The animals were observed for signs of FMD for 2 weeks. The animal receiving 2 µg of wild-type virus developed classical FMD (fever and lameness with vesicles on all four feet and the snout) within 5 days of inoculation, whereas the animal inoculated with 2 µg of the RGD-deleted virus did not show any signs of disease. As expected, radioimmunoprecipitation analyses of serum collected 28 days postinfection from the animal inoculated with the wild-type virus revealed strong reactivity to structural proteins as well as the non-structural proteins 3D and 2C, indicating that the virus had replicated in the animal (Berger et al. 1990. *Vaccine.* vol. 8, p. 213). In contrast, the 28-day postinoculation sera obtained from the pig inoculated by this route with the RGD-deleted virus showed very low levels of reactivity with structural proteins, and no detectable reactivity with non-structural proteins, indicating that the RGD-deleted virus did not replicate in this animal (Berger et al., supra).

Example 4

Inoculation of Cattle

To test the usefulness of the RGD-deleted virus as a vaccine, a vaccination/challenge study with nine 18- to 20-month-old Hereford steers was conducted. Three steers were mock vaccinated with a tissue culture media/mineral oil emulsion, three animals were vaccinated with sucrose gradient-purified, binary ethylenimine (BEI)-inactivated (H. G. Bahnemann. 1975. *Arch. Virol.* vol. 47, p. 47) wild-type virus emulsified in oil, and the remaining three animals were vaccinated with an oil emulsion containing RGD-deleted virus. Animals were observed for signs of FMD for 4 weeks, and in that time none of the animals developed fever or vesicles of FMD. Four weeks postvaccination, serum was collected from all nine animals, and tested for its ability to neutralize the virus in vitro. These assays showed that the RGD-deleted virus was indistinguishable from the BEI-inactivated preparation in its ability to elicit neutralizing antibodies in cattle (Table 3).

TABLE III

| Animal | Vaccine | Neut titer ($\log_{10}$ PRN$_{70}$) | Response to challenge | |
|---|---|---|---|---|
| | | | Fever | Lesions |
| 57 | | <0.7 | + | + |
| 109 | No vaccine | <0.7 | + | + |
| 148 | | <0.7 | + | + |
| 15 | | 3.4 | – | – |
| 103 | RGD-deleted | 2.5 | – | – |
| 143 | | 2.5 | – | – |
| 21 | | 2.5 | – | – |
| 50 | BEI-inactivated | 2.8 | – | – |
| 101 | | 2.2 | – | – |

The nine animals listed in Table 3 were combined in a single large room and exposed to a pig which had developed severe clinical manifestations of FMD after infection with a virulent cattle-passaged strain of FMDV type A$_{12}$ (Vallee strain 119, cattle passage 78; kindly provided by Dr. J. House). The cattle were examined daily for onset of clinical signs (lameness, vesicle formation on the tongue, or fever). If temperatures over 39° C. were noted, the animals were sedated and examined closely for vesicular lesions on their feet and in their mouths. All six vaccinated animals were protected from clinical disease, whereas all three mock-vaccinated animals demonstrated clinical FMD with fevers (3 days over 40° C.) and lesions on the tongue and all four feet within 7 days of exposure to the infected pig.

Effectiveness of the vaccine was further evaluated by determining if viral challenge had produced immune responses to viral antigens, i.e. by comparing the ability of pre- and postchallenge sera to precipitate viral proteins from radiolabeled infected cell lysates. For one animal (#143), a weak reaction to protein 3D was observed in prechallenge sera, consistent with the fact that antibodies to 3D are often observed in sera from vaccinated animals (Berger et al., supra). Antibodies to non-structural proteins 2C, 3AB and 3C were present in postchallenge sera of mock-vaccinated animals. Based on previously established criteria (Berger et al., supra), the presence of antibodies to two or more of these antigens demonstrates extensive viral replication, consistent with the observed clinical signs in these animals (Table 3). Several minor differences between pre- and postchallenge sera were also noted among the six vaccinated animals, and in several cases antibodies to 3D were detected in postchallenge sera. However, following challenge none of the vaccinated animals developed antibodies to 2C, 3AB or 3C, indicating that vaccination had prevented, or severely limited, viral replication (Berger et al., supra). Interestingly, one of the BEI-inactivated vaccine-vaccinated animals (#101) showed an increase in antibodies to structural proteins and the appearance of reactivity with 3D following challenge, suggesting that limited, but clearly detectable, viral replication had taken place in the face of challenge in this animal. The possibility that virus replication occurred in this animal is consistent with the finding that this animal showed the lowest prechallenge titer of neutralizing antibodies (Table 3).

This challenge study demonstrates that the RGD-deleted vaccine performed as well as, or exceeded, the accepted BEI-inactivated vaccine with respect to protection from challenge, generation of serum neutralizing antibodies, and generation of an immune response which restricts replication of the virus upon challenge. This is the first demonstration that a safe and effective vaccine can be prepared by genetically removing the cell binding site from a virus.

All references cited hereinabove are herein incorporated by reference

---

We claim:

1. A foot-and-mouth disease virus, wherein the amino acid sequence Gly-Val-Arg-Gly-Asp-Phe (SEQ ID NO: 8) from the G-H loop of VP1 has been deleted and replaced with the amino acid sequence Asn-Pro.

2. A RNA molecule comprising the genome of foot-and-mouth disease virus, wherein the sequence encoding Gly-Val-Arg-Gly-Asp-Phe (SEQ ID NO: 8) from the G-H loop of VP1 has been deleted and replaced with the sequence encoding Ash-Pro.

3. A cDNA molecule complimentary to the RNA molecule of claim 2, wherein said cDNA molecule is capable of producing a foot-and-mouth disease virus.

4. A vaccine comprising an effective immunization dosage of the virus of claim 1 and a pharmaceutically acceptable carrier or diluent.

5. A method for protecting susceptible animals from foot-and-mouth disease comprising inoculating said animals with an effective dosage of the vaccine of claim 4.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Foot and mouth disease virus ( x i ) SEQUENCE DESCRIPTION: SEQ ID NO:1:

```
Tyr Asn Gly Thr Asn Lys Tyr Ser Ala Ser Gly Ser Gly Asp Arg Gly
 1               5                  10                  15
Asp Phe Gly Ser Leu Ala Pro Arg Val Ala Arg Gln Leu Pro Ala
                20              25                  30
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Foot and mouth disease virus ( x i ) SEQUENCE DESCRIPTION: SEQ ID NO:2:

```
Tyr Asn Gly Thr Asn Lys Tyr Ser Ala Ser Gly Ser Gly Pro Arg Gly
 1               5                  10                  15
Asp Phe Gly Ser Leu Ala Pro Arg Val Ala Arg Gln Leu Pro Ala
                20              25                  30
```

( 2 ) INFORMATION FOR SEQ ID NO:3:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal (vi) ORIGINAL SOURCE:
(A) ORGANISM: Foot and mouth disease virus (xi) SEQUENCE DESCRIPTION: SEQ ID NO:3:

Tyr Asn Gly Thr Asn Lys Tyr Ser Ala Ser Gly Ser Gly Val Arg Gly
1               5                   10                  15

Asp Lys Gly Ser Leu Ala Leu Arg Val Ala Arg Gln Leu Pro Ala
            20                  25                  30

(2) INFORMATION FOR SEQ ID NO:4:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Foot and mouth disease virus (xi) SEQUENCE DESCRIPTION: SEQ ID NO:4:

Tyr Asn Gly Thr Asn Lys Tyr Ser Ala Ser Gly Ser Gly Val Lys Gly
1               5                   10                  15

Asp Phe Gly Ser Leu Ala Pro Arg Val Ala Arg Gln Leu Pro Ala
            20                  25                  30

(2) INFORMATION FOR SEQ ID NO:5:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Foot and mouth disease virus (xi) SEQUENCE DESCRIPTION: SEQ ID NO:5:

Tyr Asn Gly Thr Asn Lys Tyr Ser Ala Ser Gly Ser Gly Val Arg Gly
1               5                   10                  15

Glu Phe Gly Ser Leu Ala Pro Arg Val Ala Arg Gln Leu Pro Ala
            20                  25                  30

(2) INFORMATION FOR SEQ ID NO:6:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Foot and mouth disease virus ( x i ) SEQUENCE DESCRIPTION: SEQ ID NO:6:

Tyr Asn Gly Thr Asn Lys Tyr Ser Ala Ser Gly Ser Gly Val Arg Gly
1               5                   10                      15

Glu Phe Gly Ser Leu Ala Pro Arg Val Ala Arg Gln Leu Pro Ala
            20                  25                  30

( 2 ) INFORMATION FOR SEQ ID NO:7:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Foot and mouth disease virus ( x i ) SEQUENCE DESCRIPTION: SEQ ID NO:7:

Tyr Asn Gly Thr Asn Lys Tyr Ser Ala Ser Gly Ser Gly Val Lys Gly
1               5                   10                      15

Glu Phe Gly Ser Leu Ala Pro Arg Val Ala Arg Gln Leu Pro Ala
            20                  25                  30

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Foot and mouth disease virus ( x i ) SEQUENCE DESCRIPTION: SEQ ID NO:8:

Gly Val Arg Gly Asp Phe
1               5